United States Patent
Yang et al.

(10) Patent No.: US 11,833,205 B2
(45) Date of Patent: Dec. 5, 2023

(54) KAOLINITE COMPOSITE DIAGNOSTIC AND THERAPEUTIC AGENT AND PREPARATION METHOD AND USE THEREOF

(71) Applicant: CHINA UNIVERSITY OF GEOSCIENCES (WUHAN), Wuhan (CN)

(72) Inventors: Huaming Yang, Wuhan (CN); Juan Liao, Wuhan (CN)

(73) Assignee: CHINA UNIVERSITY OF GEOSCIENCES (WUHAN), Wuhan (CN)

( * ) Notice: Subject to any disclaimer, the term of this patent is extended or adjusted under 35 U.S.C. 154(b) by 0 days.

(21) Appl. No.: 18/055,388

(22) Filed: Nov. 14, 2022

(65) Prior Publication Data

US 2023/0149548 A1 May 18, 2023

(30) Foreign Application Priority Data

Nov. 17, 2021 (CN) .......................... 202111361897.7

(51) Int. Cl.
  *A61K 47/02* (2006.01)
  *A61K 31/275* (2006.01)
  *A61K 31/704* (2006.01)

(52) U.S. Cl.
  CPC ............ *A61K 47/02* (2013.01); *A61K 31/275* (2013.01); *A61K 31/704* (2013.01)

(58) Field of Classification Search
  CPC .... A61K 47/02; A61K 31/275; A61K 31/704; A61K 9/5115; A61K 41/0057; A61K 47/52; A61K 49/08; A61K 2300/00; A61P 35/00
  See application file for complete search history.

(56) References Cited

U.S. PATENT DOCUMENTS

| | | |
|---|---|---|
| 11,083,780 B2 | 8/2021 | Khademosseini et al. |
| 11,344,491 B2 | 5/2022 | Maibach et al. |
| 11,426,450 B2 | 8/2022 | Khademhosseini et al. |
| 2004/0213846 A1* | 10/2004 | Greenblatt ............. A01N 25/08 424/469 |

OTHER PUBLICATIONS

Yang et al. (CN108325552A Machine English Translation) (Year: 2018).*
Yi Zhang et al., Intercalated Kaolinite as an Emerging Platform for Cancer Therapy, Jan. 2019, pp. 58-61, vol. 62, Science China Chemistry, China.
Zhiming Sun et al., Enhanced Visible-light Photocatalytic Activity of Kaolinite/g-C3N4 Composite Synthesized Via Mechanochemical Treatment, Applied Clay Science, Aug. 2016, pp. 7-14, vol. 129, China.

* cited by examiner

*Primary Examiner* — Robert A Wax
*Assistant Examiner* — Quanglong N Truong
(74) *Attorney, Agent, or Firm* — True Shepherd LLC; Andrew C. Cheng

(57) ABSTRACT

The kaolinite composite diagnostic and therapeutic agent uses modified kaolinite as a carrier and is loaded with carbon nitride quantum dots and doxorubicin. The present disclosure provides a preparation method of the kaolinite composite diagnostic and therapeutic agent, including the following steps: S1: preparing the modified kaolinite by subjecting the pharmaceutical grade kaolinite to intercalation, exfoliation, and immersion wet etching; S2: subjecting the modified kaolinite and a carbon nitride quantum dot solution to ultrasonication, drying, and grinding to obtain a kaolinite composite containing the carbon nitride quantum dots; and S3: dissolving the doxorubicin in the dark, adding dissolved doxorubicin into the kaolinite composite containing the carbon nitride quantum dots, shaking in the dark for a period of time, and washing and drying to obtain the diagnostic and therapeutic agent containing the carbon nitride quantum dots and the doxorubicin.

8 Claims, 3 Drawing Sheets

KAOLINITE COMPOSITE DIAGNOSTIC AND THERAPEUTIC AGENT AND PREPARATION METHOD AND USE THEREOF

CROSS-REFERENCE TO RELATED APPLICATIONS

This application claims priority to Chinese Patent Application No. 202111361897.7 with a filing date of Dec. 17, 2021. The content of the aforementioned application, including any intervening amendments thereto, is incorporated herein by reference.

TECHNICAL FIELD

The present disclosure relates to the technical field of tumor medicines, in particular to a kaolinite composite diagnostic and therapeutic agent and a preparation method and use thereof.

BACKGROUND

Traditional cancer treatments include surgical resection, radiotherapy, and chemotherapy. The combinations of phototherapy, chemotherapy, gene therapy, and immunotherapy have been extensively studied for better tumor treatment. Chemotherapy is still the most commonly-used clinical treatment. However, chemotherapeutic drugs generally lead to weak efficacy and severe systemic cytotoxicity due to non-selective drug distribution and poor pharmacokinetics. In the past decade, rapid progress has been made in the design and development of nanoparticles as an anticancer drug carrier. However, the in vivo application of nanodrug delivery systems still faces many challenges, such as poor bioavailability, rapid systemic clearance, limited anticancer effects, and potential biosafety. Moreover, the multidrug resistance of chemotherapeutic drugs is still a concern in the treatment.

SUMMARY

In view of the above deficiencies of the prior art, the present disclosure aims to propose a kaolinite composite diagnostic and therapeutic agent and a preparation method and use thereof.

The present disclosure provides a kaolinite composite diagnostic and therapeutic agent, where the kaolinite composite diagnostic and therapeutic agent uses modified kaolinite as a carrier and is loaded with carbon nitride quantum dots and doxorubicin.

Further, the modified kaolinite is obtained by subjecting pharmaceutical grade kaolinite to intercalation, exfoliation, and immersion wet etching.

Further, the carbon nitride quantum dots are supported on a surface and inside mesopores of the modified kaolinite, and the doxorubicin is adsorbed on the surface and between layers of the modified kaolinite.

Further, the carbon nitride quantum dots are supported on the surface and inside the mesopores of the modified kaolinite in a form of nanoparticles, and the doxorubicin is adsorbed on the surface and between the layers of the modified kaolinite through electrostatic bonding.

The present disclosure further provides a preparation method of the kaolinite composite diagnostic and therapeutic agent, including the following steps:

S1: preparing the modified kaolinite by subjecting the pharmaceutical grade kaolinite to intercalation, exfoliation, and immersion wet etching;

S2: subjecting the modified kaolinite and a carbon nitride quantum dot solution to ultrasonication, drying, and grinding to obtain a kaolinite composite containing the carbon nitride quantum dots;

S3: dissolving the doxorubicin in the dark, adding dissolved doxorubicin into the kaolinite composite containing the carbon nitride quantum dots, shaking in the dark for a period of time, and washing and drying to obtain the composite diagnostic and therapeutic agent containing the carbon nitride quantum dots and the doxorubicin.

Further, in step S1, the pharmaceutical grade kaolinite is modified by stepwise intercalation with dimethyl sulfoxide and urea.

Further, in step S2, the carbon nitride quantum dots are graphite-phase carbon nitride quantum dots; and the carbon nitride quantum dot solution is prepared by the following steps: (1) conducting calcination on melamine for 2 h to 6 h to obtain a light yellow carbon nitride powder; (2) dispersing the carbon nitride powder in water at a mass-volume ratio of 1 mg:1 mL, conducting ultrasonication in an intelligent microwave catalytic synthesis extractor for 12 h to 24 h, and allowing to stand; alternatively, dispersing the carbon nitride powder in a mixture of deionized water and hydrogen peroxide, conducting ultrasonic dispersion, transferring to the reaction kettle and heating at a constant temperature for a period of time; and (3) removing large particles by centrifugation to obtain a colorless and transparent supernatant, namely the carbon nitride quantum dot solution.

Further, in step S2, the modified kaolinite and the carbon nitride quantum dot solution have a mass-volume ratio of (25-200) mg:20 mL.

Further, in step S3, the doxorubicin is placed in a PBS, dissolved by shaking in the dark, and washed with absolute ethanol; and the doxorubicin has a mass not less than that of the kaolinite composite containing the carbon nitride quantum dots.

The present disclosure further provides use of the kaolinite composite diagnostic and therapeutic agent in preparation of a drug for tumor imaging and tumor cell inhibition.

In the present disclosure, based on excellent carrier characteristics of a clay mineral kaolinite, the carbon nitride quantum dots supported on a surface of the kaolinite can play a role of dispersion and fixation, thereby preventing the agglomeration of nanoparticles. Moreover, the surface of kaolinite is hydrophilic and rich in hydroxyl groups, enabling it to have desirable interfacial bonding with the carbon nitride quantum dots, so as to achieve synergy. In addition, kaolinite can also improve the utilization and stability of drug molecules; imaging and photodynamic therapy of the carbon nitride quantum dots (CNQDs) can be effectively combined with a chemotherapeutic effect of the doxorubicin through lamellar kaolinite with a large specific surface area, realizing the combination of various treatment modes to effectively eliminate tumors.

Furthermore, interface regulation between the kaolinite and the CNQDs can promote the generation of superoxide free radicals to improve an efficiency of the photodynamic therapy. Therefore, a kaolinite composite delivery system containing the carbon nitride quantum dots and the doxorubicin provides a new platform for realizing safe and efficient combined therapy for the tumors.

Compared with the prior art, the present disclosure has the following advantages:
(1) In the present disclosure, the kaolinite composite diagnostic and therapeutic agent containing the carbon nitride quantum dots and the doxorubicin improves a photodynamic therapy effect of the carbon nitride quantum dots, improves loading and sustained release effects of the doxorubicin, and has an excellent antitumor performance.
(2) In the present disclosure, in the kaolinite composite diagnostic and therapeutic agent containing the carbon nitride quantum dots and the doxorubicin, the kaolinite carrier has no obvious cytotoxicity or hemolysis, showing desirable biocompatibility and high safety performances.
(3) In the present disclosure, the kaolinite composite diagnostic and therapeutic agent containing the carbon nitride quantum dots and the doxorubicin has abundant raw material sources and a low cost.
(4) In the present disclosure, the preparation method of the kaolinite composite diagnostic and therapeutic agent containing the carbon nitride quantum dots and the doxorubicin has simple steps and easy operation, which is conducive to large-scale production.

DETAILED DESCRIPTION OF THE EMBODIMENTS

Figure 1:
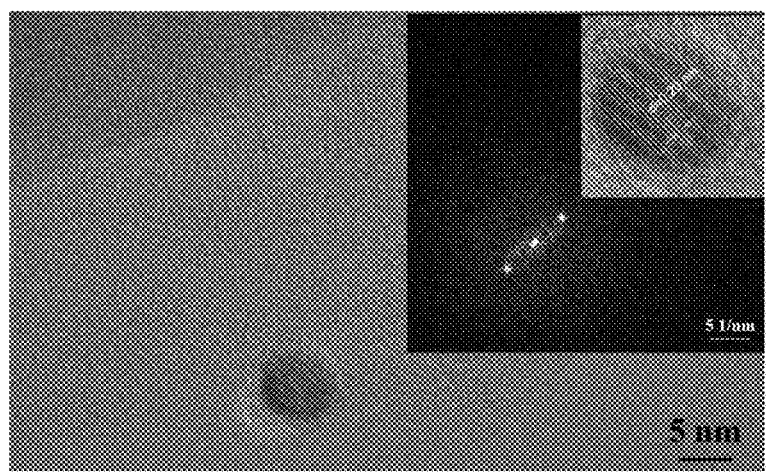
FIG. 1 shows a transmission electron microscopy (TEM) image of Kaol/CNQDs-2 prepared in Example 5.

The technical solutions of the present disclosure are described in further detail below with reference to the specific examples and accompanying drawings, but the present disclosure is not limited thereto.

The term "kaolinite" in this specification has a chemical formula of $Al_2O_3 \cdot 2SiO_2 \cdot 2H_2O$; in some forms, the kaolinite includes about 45.31% of the silica, about 37.21% of the alumina, and about 14.1% of water.

In this specification, the pharmaceutical grade kaolinite in the examples is pharmaceutical grade kaolinite from Shanghai Aladdin Biochemical Technology Co., Ltd., with a density of 2.53 g/cm³.

Preparation of Modified Kaolinite

Example 1

A preparation method of modified kaolinite included the following steps: a kaolinite intercalation compound was prepared by a step-by-step intercalation method. 90 mL of DMSO and 10 mL of deionized water were put into a reaction flask, and 10 g of pharmaceutical grade kaolinite was added into the reaction flask. A reaction was conducted by stirring for 24 h in a water bath at 60° C. After the reaction was completed, centrifugation was conducted, and an obtained precipitate was washed three times with absolute ethanol and dried at 60° C. for 24 h to obtain an intercalation complex 1, which was labeled as Kaolinite-DMSO; 39 g of urea (Urea) was added into the reaction flask, and stirred with 50 mL of deionized water until dissolved to obtain a 13 mol/L saturated urea solution. 5 g of a Kaolinite-DMSO sample was added into the above reaction flask, added with 50 mL of the urea solution, and a mixture was stirred at a room temperature for 24 h. After the reaction, centrifugation was conducted at 8,000 rpm, and an obtained precipitate was washed three times with absolute ethanol and then dried at 60° C. overnight to obtain an intercalation complex 2, which was labeled as Kaolinite-Urea; 2 g of the Kaolinite-Urea was added to 200 mL of deionized water, and subjected to ultrasonication at 100° C. for 2 h using an intelligent microwave catalytic synthesis extractor with a power of 1,000 W. After the reaction, an obtained solution was allowed to stand for 30 d, and then centrifuged at 4,000 rpm, and a supernatant was centrifuged and washed three times. A resulting solution was freeze-dried in vacuum to obtain porous kaolinite labeled as Kaolinite-Erosion.

Preparation of a Carbon Nitride Quantum Dot Solution

Example 2

(1) Carbon nitride was prepared as follows: 3 g of melamine was placed in a crucible, the crucible was sealed with tin foil and placed in a muffle furnace for calcination (calcination at 500° C. for 4 h, and then heating to 550° C. at a heating rate of 20° C., and then holding for 2 h), and a product was cooled to a room temperature to obtain a light yellow graphite-phase carbon nitride powder, marked as $g-C_3N_4$.

(2) The carbon nitride quantum dot solution was prepared as follows: 0.2 g of the $g-C_3N_4$ powder prepared in Example 2 was placed in a beaker, added with 40 mL of deionized water and 40 mL of hydrogen peroxide, and ultrasonically dispersed for 5 min; a product was poured into a reaction kettle and heated at a constant temperature for 12 h or 24 h; obtained solutions were centrifuged at 8,000 rpm for 5 min to obtain colorless and transparent supernatants, which were the carbon nitride quantum dot solutions, marked as CNQDs-12 h and CNQDs-24 h, respectively.

Example 3

A carbon nitride quantum dot solution was prepared as follows: 400 mg of the $g-C_3N_4$ powder (prepared in step (1) in Example 2) was dispersed in 400 mL of deionized water. A mixture was subjected to ultrasonication at 1,500 W for 16 h in the intelligent microwave catalytic synthesis extractor. An obtained dispersion was placed at a room temperature for 24 h, and then centrifuged at 8,000 rpm to remove large particles, so as to obtain a colorless and transparent supernatant, which was the exfoliated carbon nitride quantum dot solution, marked as CNQDs-16 h.

Preparation of a Kaolinite Composite Containing Carbon Nitride Quantum Dots

Example 4

In this example, a preparation method of a kaolinite composite containing carbon nitride quantum dots included the following steps: 100 mg of the Kaolinite-Erosion and 20 mL of the CNQDs-16 h were mixed and added to 10 mL of deionized water, stirred at 80° C. for 30 min, immersed for 2 h, centrifuged at 8,000 rpm, washed, and freeze-dried, to obtain the kaolinite composite containing carbon nitride quantum dots, labeled as Kaol/CNQDs-1.

Example 5

In this example, a preparation method of a kaolinite composite containing carbon nitride quantum dots included the following steps: 25 mg of the Kaolinite-Erosion and 20 mL of the CNQDs-16 h were placed in a petri dish and subjected to ultrasonication for 5 min in an ultrasonic cleaning apparatus. The kaolinite composite containing carbon nitride quantum dots was obtained by drying in a vacuum-drying oven at 80° C. overnight, which was labeled as Kaol/CNQDs-2.

TEM image of the carbon nitride quantum dot-containing kaolinite composite prepared in Example 5 was shown in FIG. 1.

Figure 2:
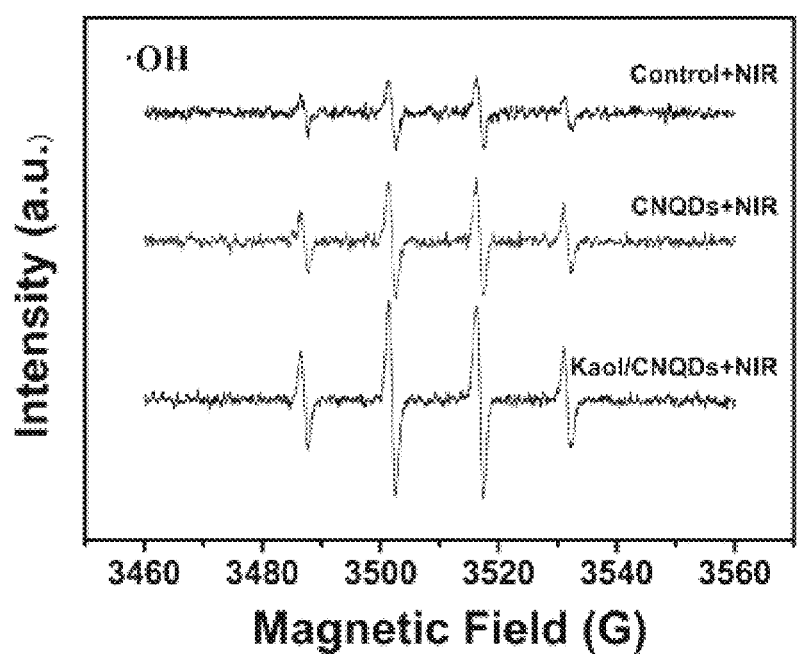
FIG. 2 show electron paramagnetic resonance spectra of the Kaol/CNQDs-2 prepared in Example 5, and the ability to generate OH is shown.

The electron spin-resonance (ESR) images of the carbon nitride quantum dot-containing kaolinite composite prepared in Example 5 were shown in FIG. 2.

FIG. 1 showed the topography of Kaol/CNQDs-2, with small particles of carbon nitride quantum dots dispersed and supported on kaolinite.

FIG. 2 was the electron paramagnetic resonance spectra of Kaol/CNQDs-2, and abilities to generate OH.

FIG. 2 illustrated that the CNQDs could generate reactive oxygen species, ·OH under laser irradiation at 670 nm, while the Kaol/CNQDs-2 had a higher ability to generate active species than the CNQDs, indicating that Kaol could promote the production of active species.

Preparation of a Kaolinite Composite Diagnostic and Therapeutic Agent Containing Carbon Nitride Quantum Dots and Doxorubicin

Example 6

In this example, a method for loading doxorubicin on a kaolinite composite containing carbon nitride quantum dots included the following steps: 1.580 g of NaOH was added to 395 mL of deionized water to prepare a 0.1 mol/L NaOH solution. The NaOH solution was added with 6.805 g of $KH_2PO_4$, and then diluted to 1,000 mL with water to obtain a PBS at pH=7.4.

30.3 mg of doxorubicin hydrochloride was added to 60 mL of the PBS (pH=7.4), stirred well and subjected to ultrasonication until dissolved. 25.2 mg of the Kaol/CNQDs-2 was added, shaken at 37° C. in the dark for 24 h, washed with absolute ethanol three times, and dried at 60° C. for 24 h to obtain the kaolinite composite containing carbon nitride quantum dots and doxorubicin, labeled as Kaol/CNQDs/DOX.

Example 7

In this example, a method for loading doxorubicin on a kaolinite composite containing carbon nitride quantum dots included the following steps: 1.580 g of NaOH was added to 395 mL of deionized water to prepare a 0.1 mol/L NaOH solution. The NaOH solution was added with 6.805 g of $KH_2PO_4$, and then diluted to 1,000 mL with water to obtain a PBS at pH=7.4.

30.1 mg of doxorubicin hydrochloride was added to 60 mL of the PBS (pH=7.4), stirred well and subjected to ultrasonication until dissolved. 25.0 mg of the Kaol/CNQDs-2 was added, shaken at 37° C. in the dark for 24 h, washed with absolute ethanol three times, and dried at 60° C. for 24 h to obtain the kaolinite composite containing carbon nitride quantum dots and doxorubicin, labeled as Kaol/CNQDs/DOX.

Example 8

In this example, a method for loading doxorubicin on a kaolinite composite containing carbon nitride quantum dots included the following steps: 1.580 g of NaOH was added to 395 mL of deionized water to prepare a 0.1 mol/L NaOH solution. The NaOH solution was added with 6.805 g of $KH_2PO_4$, and then diluted to 1,000 mL with water to obtain a PBS at pH=7.4.

30.0 mg of doxorubicin hydrochloride was added to 60 mL of the PBS (pH=7.4), stirred well and subjected to ultrasonication until dissolved. 24.7 mg of the Kaol/CNQDs-2 was added, shaken at 37° C. in the dark for 24 h, washed with absolute ethanol three times, and dried at 60° C. for 24 h to obtain the kaolinite composite containing carbon nitride quantum dots and doxorubicin, labeled as Kaol/CNQDs/DOX.

Figure 3:
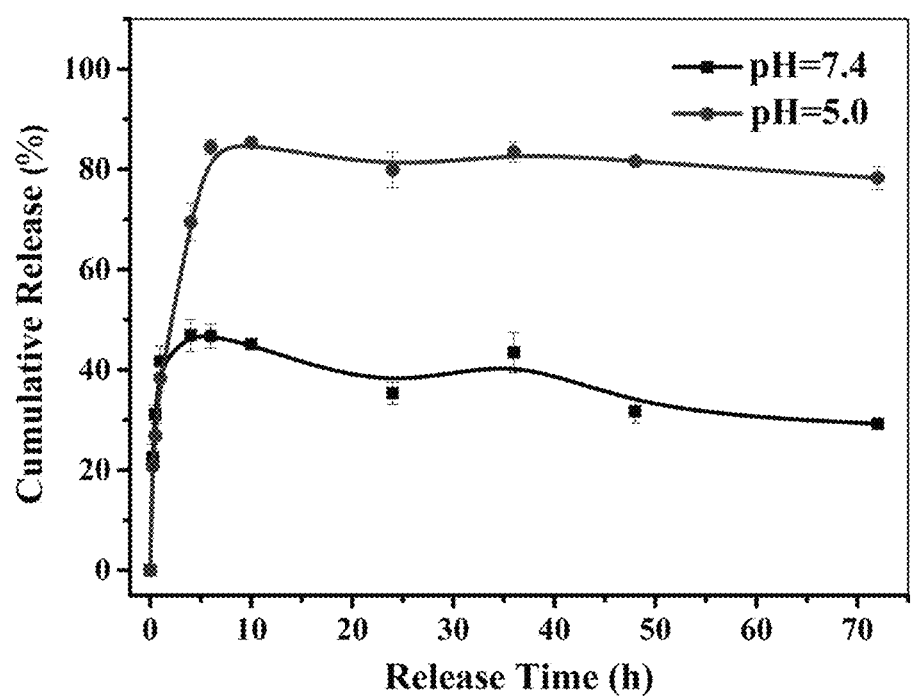
FIG. 3 shows a drug release curve of Kaol/CNQDs/DOX prepared in Examples 6 to 8 after mixing.

The materials prepared in Examples 6 to 8 were mixed, and a drug release curve of a resulting mixed material to doxorubicin was shown in FIG. 3. It was seen from FIG. 3 that the Kaol/CNQDs/DOX prepared in Examples 6 to 8 could achieve pH-responsive release, and could achieve a cumulative release rate of more than 80%, improving the utilization rate of the drug.

Cytotoxicity Assay

Human immortalized epidermal cells (HaCaT, Department of Biochemistry and Molecular Biology, School of Life Sciences, Central South University) were selected as a subject. Human venous endothelial cells were cultured with a 1640 medium, specifically a mixture of 10% fetal bovine serum and 1% penicillin-streptomycin. The HaCaT cells were cultured in a sterile environment at 37° C. with 5% $CO_2$. A fresh medium was replaced every two days until the cells reached an appropriate degree of aggregation. Each well plate was inoculated with 100 µL of a cell suspension, cultured for 12 h to a concentration of $2 \times 10^4$ cells/mL, and the kaolinite composite at a concentration of 500 µg/mL was added to a 96-well plate, and incubated for 12 h. The old medium was precipitated, 100 µL of a CCK8 solution was injected into each well plate, and the cells were cultured for 4 h. Once the culture was completed, a supernatant was removed, and 100 µL of the medium was added. After culturing for 1 h, an absorbance was measured with a microplate reader (at 450 nm), and three parallel experiments were set up. A blank control group was set up without the kaolinite composite. The cytotoxicity results of the cases were shown in Table 1.

TABLE 1

| | Cytotoxicity results | |
|---|---|---|
| Example | Material | Cell viability (%) |
| Control group | No kaolinite composite | 100.00 ± 3.42 |
| Example 1 | Kaolinite-Errosion | 213.75 ± 25.43 |

The blank control group and the Kaolinite-Erosion had cell viability of 100.00±3.42% and 213.75±25.43, respectively. Under this condition, kaolinite even promoted cell proliferation, indicating that the kaolinite prepared by intercalation, exfoliation, and immersion wet etching had desirable biocompatibility when being used as a carrier.

Drug Loading Test:

30 mg of doxorubicin hydrochloride was added to 60 mL of the PBS (pH=7.4), stirred well and subjected to ultrasonication until dissolved. 25 mg of the Kaol/CNQDs-2 was added, shaken at 37° C. in the dark for 24 h, washed with absolute ethanol three times, and dried at 60° C. for 24 h to obtain the kaolinite composite containing carbon nitride quantum dots and doxorubicin, labeled as Kaol/CNQDs/DOX.

The Kaol/CNQDs-2 had a drug loading rate of 41.38±0.56% and an encapsulation rate of 75.86±1.02% for doxorubicin. This indicated that the kaolinite composite containing carbon nitride quantum dots had high bioavailability of doxorubicin and was an ideal carrier for doxorubicin drugs.

What is not mentioned above can be acquired in the prior art.

While some specific embodiments of the present disclosure have been described in detail by way of examples, those skilled in the art will appreciate that the above examples are provided for illustration only and not for the purpose of limiting the scope of the present disclosure. A person skilled in the art can make various modifications or supplements to the specific embodiments described or replace them in a similar manner, but it may not depart from the spirit of the present disclosure or the scope defined by the appended claims. Those skilled in the art should understand that any modification, equivalent replacement, and improvement that are made to the above embodiments according to the technical essence of the present disclosure shall be included in the protection scope of the present disclosure.

What is claimed is:

1. A kaolinite composite diagnostic and therapeutic agent, wherein the kaolinite composite diagnostic and therapeutic agent comprises a carrier, wherein the carrier comprises modified kaolinite and the carrier is loaded with carbon nitride quantum dots and doxorubicin;
wherein the modified kaolinite is obtained by subjecting pharmaceutical grade kaolinite to intercalation, exfoliation, and immersion wet etching and the modified kaolinite comprises mesopores; and the carbon nitride quantum dots are supported on a surface and inside the mesopores of the modified kaolinite, and the doxorubicin is adsorbed on the surface and between layers of the modified kaolinite.

2. The kaolinite composite diagnostic and therapeutic agent according to claim 1, wherein the carbon nitride quantum dots are supported on the surface and inside the mesopores of the modified kaolinite in a form of nanoparticles, and the doxorubicin is adsorbed on the surface and between the layers of the modified kaolinite through electrostatic bonding.

3. A preparation method of the kaolinite composite diagnostic and therapeutic agent according to claim 1, comprising the following steps:
S1: preparing the modified kaolinite by subjecting the pharmaceutical grade kaolinite to intercalation, exfoliation, and immersion wet etching;
S2: subjecting the modified kaolinite and a carbon nitride quantum dot solution to ultrasonication, drying, and grinding to obtain a kaolinite composite containing the carbon nitride quantum dots;
S3: dissolving the doxorubicin in the dark, adding dissolved doxorubicin into the kaolinite composite containing the carbon nitride quantum dots, shaking in the dark for a period of time, and washing and drying to obtain the composite diagnostic and therapeutic agent containing the carbon nitride quantum dots and the doxorubicin.

4. The preparation method according to claim 3, wherein in step S1, the pharmaceutical grade kaolinite is modified by stepwise intercalation with dimethyl sulfoxide and urea.

5. The preparation method according to claim 3, wherein in step S2, the carbon nitride quantum dots are graphite-phase carbon nitride quantum dots; and the carbon nitride quantum dot solution is prepared by the following steps: (1) conducting calcination on melamine for 2 h to 6 h to obtain a light yellow carbon nitride powder; (2) dispersing the carbon nitride powder in water at a mass-volume ratio of 1 mg:1 mL, conducting ultrasonication in an intelligent microwave catalytic synthesis extractor for 12 h to 24 h, and allowing to stand; alternatively, dispersing the carbon nitride powder in a mixture of deionized water and hydrogen peroxide, conducting ultrasonic dispersion, transferring to the reaction kettle and heating at a constant temperature for a period of time; and (3) removing large particles by centrifugation to obtain a colorless and transparent supernatant, namely the carbon nitride quantum dot solution.

6. The preparation method according to claim 5, wherein in step S2, the modified kaolinite and the carbon nitride quantum dot solution have a mass-volume ratio of (25-200) mg:20 mL.

7. The preparation method according to claim 3, wherein in step S3, the doxorubicin is placed in a PBS, dissolved by shaking in the dark, and washed with absolute ethanol; and the doxorubicin has a mass not less than that of the kaolinite composite containing the carbon nitride quantum dots.

8. Use of the kaolinite composite diagnostic and therapeutic agent according to claim 1, comprising applying the kaolinite composite diagnostic and therapeutic agent to implement tumor imaging and tumor cell inhibition.

* * * * *